United States Patent [19]

Schwarzmann et al.

[11] Patent Number: 4,969,864
[45] Date of Patent: Nov. 13, 1990

[54] VENTICULAR ASSIST DEVICE

[76] Inventors: Frank Schwarzmann, 4151 Elmwood Rd., Colgate, Wis. 53017; Michael J. Scharzmann, 1341 Meyati Ct., Hubertus, Wis. 53033

[21] Appl. No.: 370,663

[22] Filed: Jun. 23, 1989

[51] Int. Cl.$^5$ ............................................. A61N 1/362
[52] U.S. Cl. ................................. 600/16; 128/DIG. 3
[58] Field of Search ............... 600/16, 17; 128/DIG. 3

[56] References Cited

U.S. PATENT DOCUMENTS

| | | | |
|---|---|---|---|
| 2,954,738 | 10/1960 | DiVette | 417/383 |
| 4,167,046 | 9/1979 | Portner et al. | 128/DIG. 3 |
| 4,222,127 | 9/1980 | Donachy et al. | 417/394 |
| 4,293,961 | 10/1981 | Runge | 417/412 |
| 4,384,829 | 5/1983 | Conley et al. | 417/412 |
| 4,457,673 | 7/1984 | Conley et al. | 417/412 |
| 4,488,099 | 12/1984 | LaForge et al. | 318/561 |
| 4,524,466 | 6/1985 | Hall et al. | 600/16 |
| 4,557,673 | 12/1985 | Chen et al. | 128/DIG. 3 |
| 4,565,497 | 1/9186 | Miller et al. | 128/DIG. 3 |

*Primary Examiner*—Lee S. Cohen
*Assistant Examiner*—Scott M. Getzow
*Attorney, Agent, or Firm*—Wheeler Law Firm

[57] ABSTRACT

A blood sac for a heart assist device having pump pusher plates attached to its sides and an actuator system that is pivotally attached to the plates. The actuator mechanism has a movable fulcrum and levers. The movable fulcrum allows the levers of the actuator mechanism to move the pump pusher plates in a straight line toward and away from each other. The actuator mechanism allows the heart assist device to pump blood through any valve or parts of the heart to which it may be attached. The actuator mechanism allows full stroke variable speed to be imparted to the pump pusher plates. The actuator mechanism allows continuous active filling of the blood sac. The actuator mechanism is powered by a toroidally wound brushless DC motor, the speed of which is controlled by a microprocessor based upon information supplied to the microprocessor from a sensor.

14 Claims, 3 Drawing Sheets

VENTICULAR ASSIST DEVICE

BACKGROUND OF THE INVENTION

The present invention relates to the field of heart pump and heart assist devices. Specifically the present invention is a heart pump which is used to assist a patient's heart thereby reducing the strain under which it works. The invention is a ventricular assist device of a unique and simple design.

The inventor knows of no prior art heart assist device (the device) which accomplishes the functions or has the structure of the invention disclosed herein. For example U.S. Pat. No. 2,954,738 (DiVette) shows both a flat diaphragm and a cylindrical diaphragm for pumping blood. The flat diaphragm is driven by a cam, and the cylindrical diaphragm is symmetrical. Other than that there is no similarity between DiVette and the invention disclosed by the applicant. Further, U.S. Pat. No. 4,167,046 (Portner) shows a bag to do the pumping and a plate 17 on either side which appears to be pushed inward symmetrically; please see FIG. 2 of the Portner patent. The plates 17 never quite touch and the deformation of the sack is low. The actuator is a solenoid 33 which is coupled by means of a spring. Neither the solenoid nor the spring are present in the applicant's device. U.S. Pat. No. 4,222,127 (Donachy) uses a blood sac which is compressed by a diaphragm. The diaphragm appears to be driven by alternate vacuum pluses and the pressure pluses from the control unit. None of the balanced driving structure that is in the applicant's device is shown in Donachy. U.S. Pat. No. 4,293,961 (Runge) shows a mechanism which has little in common with the applicant's invention and which is intended for heart by-pass operations only. U.S. Pat. No. 4,384,829 (Conley) shows a blood pumping bag and plates 15 which are similar to the applicant's invention. The plates are driven by levers, however, the pivots of the levers are fixed and are driven by solenoid coils. This is different from the applicant's invention. U.S. Pat. No. 4,488,099 (LaForge) shows what appears to be the same mechanism as disclosed in Conley but the emphasis in the patent is on the control of the speed, acceleration, etc. of the pumping stroke. U.S. Pat. No. 4,557,673 (Chen) likewise shows a blood pumping bag and the plates 34 that compress it from the sides. Like the previous patents the plates are mounted on lever arm with fixed pivots and solenoid coils to drive them. The emphasis of Chem is on the formation of the sac itself. U.S. Pat. No. 4,457,673 (Conley) again shows substantially the same mechanism but the emphasis appears to be on the fact that the lever that actuates the pusher plate is in fact a long leaf spring, giving desirable characteristics to the pump motion. This is not the same as the applicant's invention. U.S. Pat. No. 4,565,497 (Miller) again shows a similar mechanism driven by solenoids and using levers which are springs. There are additional pre-load springs. There is no hint of the use of symmetrical motion, linear bearings, or cam followers. Further, there is no hint of the applicant's lever arms which are driven in a linear path at lower end to move the middle lever pivot up a slot to impart linear movement to the top end of the lever connected to the pusher plates.

Finally, the pumping action of the applicant's invention, unlike prior devices of a similar nature, does not pump blood through the heart in high pressure spurts but rather allows the pump stroke of the heart assist device to begin gradually in order to allow the valves of the device to be activated less forcefully.

SUMMARY OF THE INVENTION

The device shown and described herein can be either a partial or a complete support for the blood circulation of a patient.

It is the objective of this invention to provide full stroke variable speed to both systolic and diastolic strokes of the heart assist device.

Our ventricular assist device is powered by a miniature electric motor that moves an actuator mechanism which allows a pushing as well as pulling action upon a dual pusher plate blood sac. The pulling action makes it an actively filling device. It allows augmentation of filling pressure during the fill phase of the cardiac cycle (diastole) to improve upon inadequate filling conditions. Such conditions can arise when the device is connected to the atrium of the heart where it needs to complete with the ventricle for adequate blood supply or where blood is returning from the pulmonary circulation at an inadequate flow rate.

Actuator: Our actuator mechanism is a major change which gives uniqueness to this device. During systole, motor torque is being transformed to thrust force by way of end-jointed linkages connecting the motor shaft with a dual-shafted dual reciprocator. Linkages couple eccentrically with motor shaft axis. The reciprocator shafts connect with the angled actuating arms of pusher plates for transfer of force to the blood pump. The actuating arms, pivoting in slotted frame supports product linear force action upon the pusher plates at an angle of 90° with the midline of the pump. During diastole, when the motor reverses direction, the reverse process of force transformation takes place. A small negative force (slightly less than atrial pressure) is being applied to the pump plates. The reciprocators (two miniature-stroke-ball-be with their shafts jointed for load distribution and single stroke length) are firmly attached by their ways to the VAD frame. Long-life, stable performance with out stick slip is obtainable with these high accuracy compact-sized miniature-stroke-ball-bearings of superior dimensional tolerance.

Our device automatically regulates itself to circulatory blood flow conditions. It adjusts its outflow to changes in inflow by acting at a variable rate with full stroke volume. Its variable rate sensitivity arises: (1) from the inverted negative pressure (sac-pulling action) reducing fill time of the pump during diastole and (2) from motor speed adjustment based on a transducer-derived blood pressure signal.

Maintaining full stroke volume pumping flushes all of the blood pump internal surfaces with blood during each cycle, causing minimization of blood clot forming tendencies due to the good washing action of a full flowing pump.

Our device, with the type of electric motor described, allows minimization of initial pressure gradients when the sac is under compression to guard against valve and blood component damage. Such control is accomplished with the control circuitry which generates the desired velocity signal that follows the velocity profile versus displacement curve, a path of predetermined shape.

High pressure gradients, especially at the beginning of a cycle, can injure valves in the natural heart or in the assist device. They also cause stress damage in the arteries and veins, and may injure cellular components of the blood.

CONTROL: Control of our ventricular assist device has as its objective the automatic adjustment of pump outflow responding to a change of inflow by adjusting the speed of the variable-rate motor while maintaining full-stroke volume. It enables the pump to respond in a sensitive manner to an increase in atrial pressure by delivering an increased output while remaining relatively independent on afterload (arterial pressure). Pump action producing a full stroke volume provides efficiency and can lead to a better washing action and reduction of thrombus formation. A rate of approximately 130 beats per minute with a stroke volume of 70 ccm into a pressure of approximately 120 mmHg can be achieved under peak system function. Control of the unit is carried out by an electronic system with a methodology that is based on proven motor and motion-control technology. The system performs the function of Position Sensing, Commutation, Power Switching and Control. The relation of these to the complete system is shown in FIG. 11.

System Sensing Provides motor information to the commutation and control subsystem in the form of a signal proportional to pusher plate position. The exact sensor type is optional, as described later.

Commutation assures that proper angular separation between the rotor and stator magnetic fields is maintained. This is done by application of power to the windings in a pattern determined by rotor position and direction of torque. It is performed by a known electronic circuit. A microprocessor and a read-only-memory or custom I.C. are circuit's main components. Inputs to the circuit are motor position, direction and pulse-width modulation. The duty cycle of the pulse width modulation is the desired duty cycle of the motor current. The ROM contents can be thought of as a table, listing the commutation code versus motor position (together with direction and pulse-width).

Power Switching The output circuit responds to the control signal by applying current to the motor windings in the manner specified by the commutation code. Control generates the desired velocity signal which follows the velocity profile versus displacement curve, a path of predetermined shape, as shown in FIG. 10. Its purpose is to minimize inertial forces and maximize efficiency. It must shape motor motion to limit momentum during reciprocation to avoid harmful stresses to the sac and prosthetic valves, and in addition, adjust stroke speed in relation to solid state transducer-monitored mean atrial pressure. The result is smooth mechanical actuation that produces a force in both directions (pulling as well as pushing the sac). Atrial filling pressure is thus augmented during diastole with mild suction applied, and the variable-rate feature, dependent primarily on atrial pressure, is realized.

Another part of the Control is known synchronization system to allow the pump to be synchronized to the natural heart, if desired.

Energy Converter

A small brushless DVC motor of proven conventional design and made from rare-earth magnetic material combines high performance with long-life reliable operation for smooth electro-mechanical power transformation.

Blood Pump

The blood pump is very similar to the NOVA CORE VAD pump. It has a blood sac made from blood compatible biomer material with tangential inflow/outflow conduits containing the unidirectional prosthetic valves. The two symmetrically opposed pusher plates act upon the sac in a balanced force motion that results in superior blood flow-through patterns, which are essentially free from fluid statis, separation, momentum transfer and turbulence. Sac bending stresses that can lead to calcification and deterioration are minimized and prosthetic valve vibration is essentially eliminated.

Control

Control of the device is envisioned to be automatic. Pump inflow pressure signal detection along with microprocessor executed electronic control methodology, provide the device with self-regulatory response to inflow variation., Motor stator windings are thus energized from a voltage inflow variations. Motor stator windings are thus energized from a voltage waveform that provides the rotor with the necessary speed, angle of limited rotation, bidirectionality, torque and efficient use of power.

A further objective is to provide a heart assist device that can be intercannulated either at the ventricular apex or atrium of the heart. The device may be implanted subcutaneously in the left upper quadrant of the abdomen of the patient. The device is intended to temporarily support or partially support the systemic circulation, thereby serving as either a bridge until a heart transplant may be performed or as a means by which the patient may kept alive while his heart heals itself.

It is a further object of this invention to provide a variable rate to the speed of the pump compression and expansion in order to limit the initial pressure radient of the blood flow and minimize blood acceleration, thereby allowing the valves of the heart assist device a chance to seal themselves more naturally and prevent damage or limit long term wear.

It is also the objective of the invention to provide continuous active cycling of blood through the blood sac.

The heart assist device is designed for either singular right or left heart or biventricular support, using two devices. For example, the device will take the blood from the patient's left ventricle or atrium and will pump it to the patient's aorta. By doing so the heart of the patient becomes either fully or partly unloaded, because the blood is being removed as the patient's heart pumps. Further, because of the manner in which the device functions the heart itself is kept full of blood with every beat. This means that every surface of the heart and heart assist device that is exposed to blood is continually washed with blood thereby minimizing clot formation that can occur in the heart assist devices.

The electronics that control the stroke of the invention are not shown except schematically and are not part of the invention. However, known circuits associated with the applicant's invention will either detect the EKG signal sent by the patient's own body to initiate the heart beat, or detect pump inflow (atrial) pressure, and known circuits may use either or both pieces of information to synchronize and regulate the action of the electric motor that drives the ventricular assist device and/or adjust its speed, thereby providing the device with self-regulatory variable response to inflow variations; i.e. the speed at which a full stroke is made by the heart assist device is variable; further, the speed is variable during the course of the stroke itself.

It is for these reasons that the particular type of rotary reversible DC motor disclosed herein is used. The motor can be readily controlled as to speed during the systole and the diastole strokes. The rate at which the device operates will increase at the same rate as the patients's heartbeat because the synchronizing signal is either (or both) the one used by the patient's own heart (usually referred to as the R wave of an electrocardiogram), or a measure of atrial pressure. Not only does this give the heart more help, but it makes certain that the blood is being removed just ahead of the natural beat of the heart so that the heart meets as little resistance a possible, enhancing the effectiveness of the assist device and allowing the heart to pump blood with the least amount of burden. Also, the electronic sensing allows for variable adjustment of the stroke speed of the DC motor. This means that smooth mechanical actuation will produce a force in both directions that pulls as well as pushes the walls of the blood sac. Atrial pressure during diastole will thus be augmented by a mild suction that is produced by the pulling force that occurs when the pusher plates at the sides of the blood sac move apart positively.

The purpose of the control system and sensors is to minimize inertial forces and maximize efficiency of the pumping action. The control signals, in addition to controlling the speed of the systole and diastole strokes, must shape the motor motion to limit momentum during reciprocation (the point at which the DC motor reverses direction, see infra) to avoid harmful stresses to the blood sac and prosthetic valves of the ventricular assist device.

The device includes a known type of blood sac and valves used in other heart assist devices. However, the sac is squeezed from both sides by parallel plates moving in a linear direction and the squeezing action imparted to the pusher plates during systole is gradual; starting with a small initial force that allows the valves to seat themselves, increasing to a maximum squeezing pressure, and then decreasing gradually back to zero. The process if reversed for diastole. Represented graphically both processes would look similar to a bell shaped curve. Squeezing from one side alone requires much longer travel of the squeezing element and requires parts of the bag to roll substantially with respect to other parts. Further, an actuating arm or lever is used to move the pump pusher plates. The lever is pivoted near its center. Normally pushing on one end of a lever will cause the other end of the lever to move in an arc. This must be avoided because such movement will distort the blood sac. Also, if the pusher plates were fixed to the upper ends of the levers the upper end of the pusher plates would come together, killing blood cells where they contacted each other. To avoid this the pusher plates are attached to the levers by pivots. If this were the only modification then the end of the lever would move in an arc that would pull down the sides of the blood sac, distorting it in the frame. However, the unique design of the actuator mechanism wherein the pivot point of fulcrum of the lever moves, prevents this from happening. Two actuators are disclosed which are capable of moving the levers in the required manner.

During systole, motor torque is gradually transformed to thrust force by way of L-ball jointed linkages that connect the motor shaft with the dual-shafted reciprocators; the reciprocators are two miniature linear stroke ball bearings with their shafts joined for load distribution and stability. The L-ball linkages are coupled eccentrically with the motor shaft axis on one end and the reciprocator shafts on the other. The reciprocating shafts are connected with the angled actuating levers for the pusher plates to transfer the force of the motor to the pusher plates that are attached to the blood sac. The actuating levers each have a fulcrum that pivots and slides in a slotted frame. The lower end of each actuating lever is connected to a reciprocating shaft. The reciprocating shafts ride into an out of sleeves containing linear miniature stroke ball bearings. The linear miniature stroke ball bearings are at 90° angles to the midline of the device. This angle causes the lower end of each actuating lever to move in a straight line as the motor runs. Simply put, as the lower end of each reciprocator moves in straight line during systole, the fulcrum pivot point that's trapped in the slotted frame must rise. Since the moveable pivot point of the lever acts as the fulcrum the straight line motion of the lower ends of the levers is imparted to the top ends of the levers. The result is that the motion of the upper ends of the levers that are attached by pivots to the pusher plates is a straight linear motion. This means that the two pusher plates remain parallel and move directly toward each other along their common center line and evenly compress the blood sac without allowing the sides of the blood sac to distort or come close enough for damage to blood cells to occur. During diastole, when the motor reverses direction, the reverse process of force transformation takes place. A small negative force (slightly less than atrial pressure) is applied to the pump plates as the lower ends of the levers are pulled toward the central shaft of the DC motor. As the pump plates are pulled apart, again in a straight line, the mild suction produced causes active filling of the blood sac. This active filling greatly improves blood pump filling and removes blood that would otherwise place a load on the natural heart. Because the miniature linear stroke ball bearings allow only an extremely small amount of friction, long life and stable performance without stick slip is obtained for the ventricular assist device.

Control of the stroke of the DC motor is maintained by means of a known microprocessor that contains a commutation code. The microprocessor has an EPROM (Erasable Programmable Read Only Memory) chip or other custom I.C. that will maintain its memory even if the power should fail. The commutation code acts as a source book for the microprocessor providing directions that tell the motor what to do in response to data from the sensor(s) about the heart rate and/or atrial pressure. Based on this information the microprocessor is able to vary the speed of the stroke of the DC motor during the stroke itself by varying the current supplied to the motor during the stroke. Further, the commutation code ensures that proper separation between the rotator and stator magnetic fields of the motor is maintained. The microprocessor maintains the synchronization of the blood pump action with the heart's own pumping action. However, should the heart go into an abnormal pumping action such as fibrillation the synchronous control of the pump may be over-ridden and the pump may be directed to pump blood at a fixed rate.

An alternate, less preferred form of our device uses an actuator in which the motor shaft carries a cam, and the actuator lever for the pusher plates has a cam follower at the lower end. The cam follower rides a ramp shaped to displace the lever just enough so that the upper end follows a straight line toward the upper end of the other lever. As in the preferred form, the fulcrum is displaced to accommodate this movement.

It is the objective of the applicant to create a ventricular assist device that provides good blood flow characteristics with good energy use and ease of control. Because the ventricular assist device allows active filling, it can be inflow connected to the atrium as well as the ventricle. The device can, therefore, service as an indefinite circulatory support or as a bridge to transplantation. A simple but unique actuating mechanism is used to convert the motion of the DC motor to a linear pusher plate stroke motion.

The specific structure of the device is set forth in the following detailed description.

DESCRIPTION OF THE DRAWINGS

All views are shown prior to encapsulation.

FIG. 6 is a side elevational view of the alternate embodiment of the heart assist device.

FIG. 7 is a side elevational view of the alternate embodiment of the heart assist device showing the configuration of the plates in systole.

FIG. 8 is a front elevational view of the heart assist device in its alternate form.

FIG. 9 is a view from line 9—9 of FIG. 7.

DETAILED DESCRIPTION

Although the disclosure hereof is detailed and exact to enable those skilled in the art to practice the invention, the physical embodiments herein disclosed merely exemplify the invention which may be embodied in other specific structure. While the preferred embodiment has been described, the details may be changed without departing from the invention, which is defined by the claims.

Figure 1:
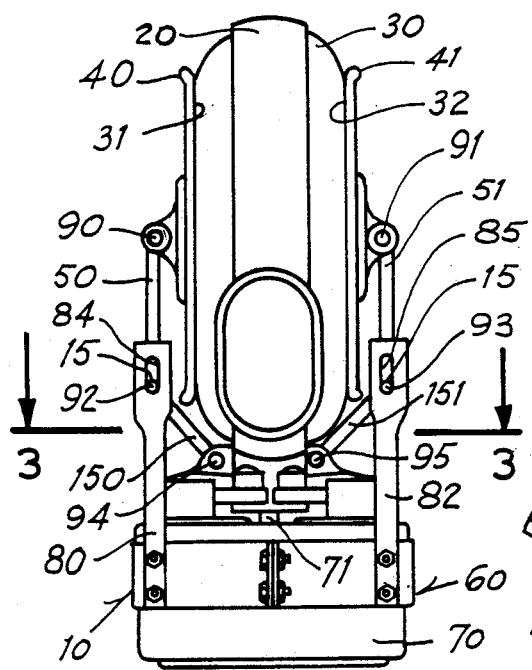
FIG. 1 is a side elevational view of the preferred form of our ventricular assist device.
Figure 2:
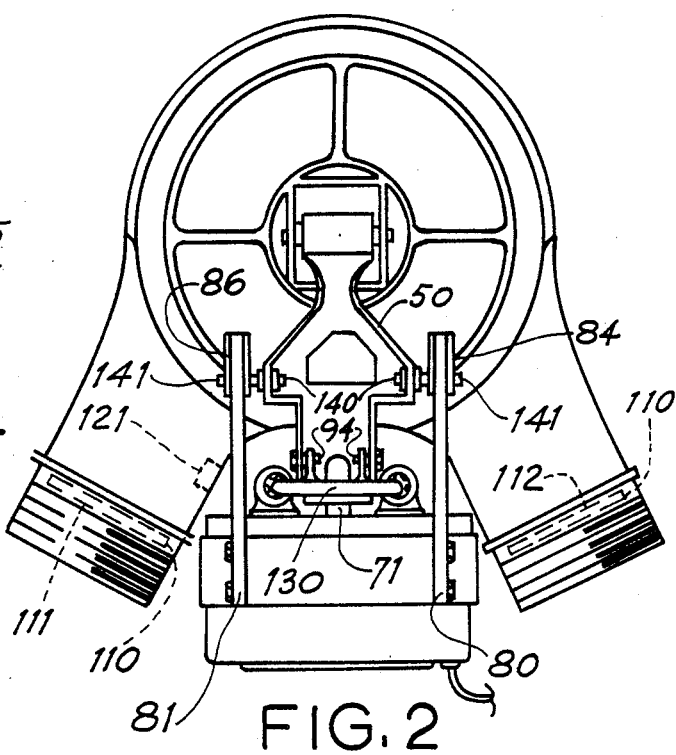
FIG. 2 is a front elevational view of the ventricular assist device showing the blood sac compressed.
Figure 4:
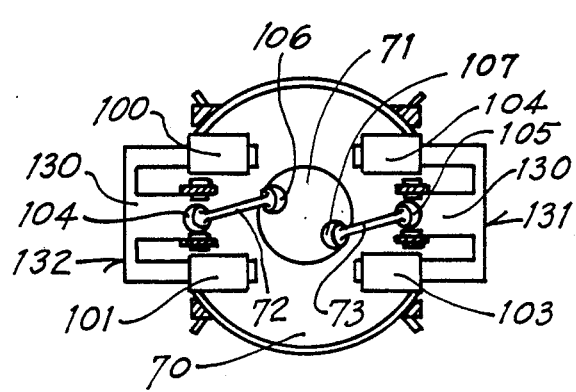
FIG. 4 is a view from line 4—4 of FIG. 5.
Figure 11:
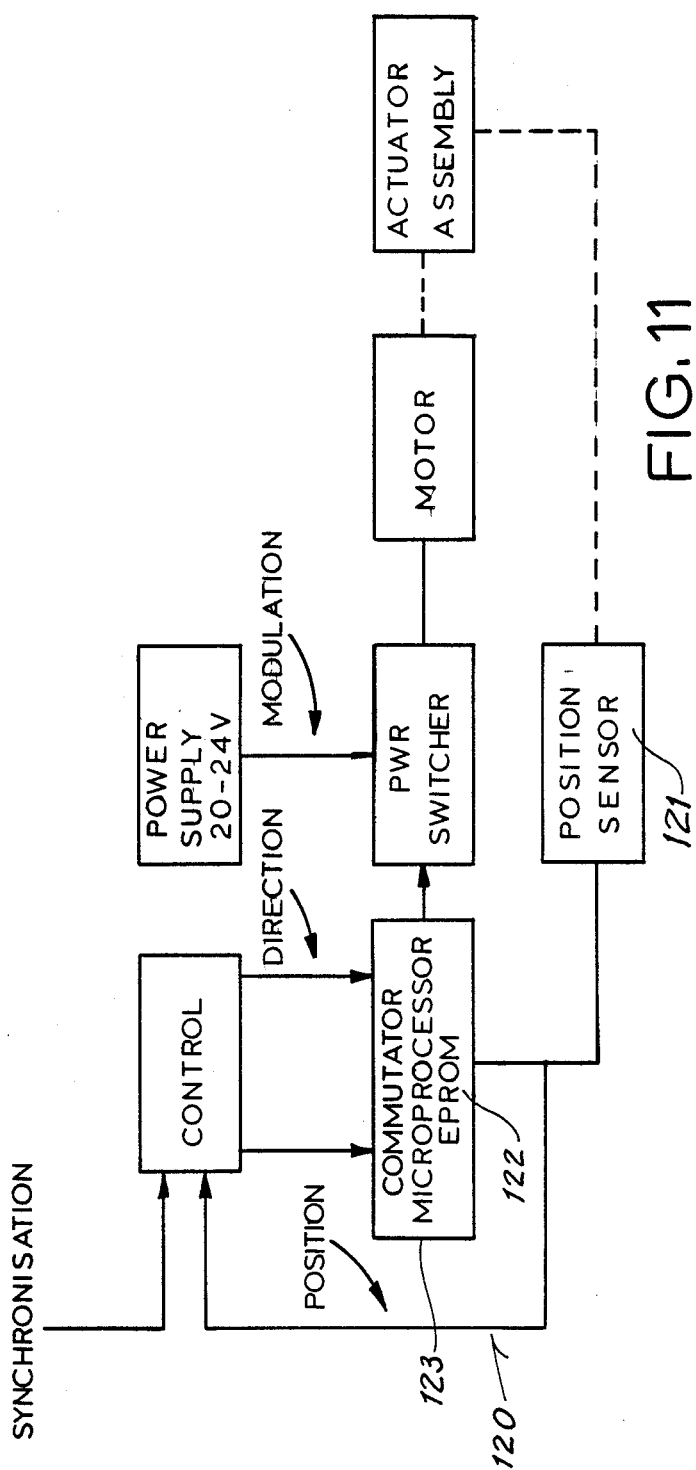
FIG. 11 is a schematic drawing showing the relationship of the sensor, computer, and heart assist device components.

Referring to FIGS. 1, 2 and 4, the heart assist device 10 may be seen to be comprised of a pump frame 20, a blood sac 30, two pusher plates 40 and 41, two actuating lever arms 50 and 51, a metallic mounting ring 60, a brushless toroidally wound rotary DC motor 70, a motor shaft 71, two link arms 72 and 73, two pairs of slotted arm support struts 80 through 82 (and one which is not shown) having slots 84 and 85 (the remaining corresponding slots are not shown), two needle bearings 90 and 91, four sets of needle bearings 92-95, two E-shaped reciprocators 130 and 131 having four linear miniature stroke ball-bearings 100 through 103, four L-ball-linkages 104 through 107, a valve housing 110 containing two valves 111 and 112, and a computer control circuit 120 (please see FIG. 11).

Referring to FIGS. 1 through 5 the relationship of the various parts of the heart assist devices 10 may be seen. The blood sac 30 is supported by the pump frame 20. The blood sac 30 is generally circular and has parallel flat sides 31 and 32 which are attached to pump pusher plates 40 and 41, respectively. Actuating levers 50 and 51 are attached to pump pusher plates 40 and 41 by needle bearings 90 and 91, respectively. Actuating levers 50 and 51 are bent at an angle that is necessary to fit within the unit in all positions. The points at which each actuating levers 50 and 51 are bent carries a moveable fulcrum 15. These points are also the location of needle bearings 92 and 93, respectively.

Figure 6:
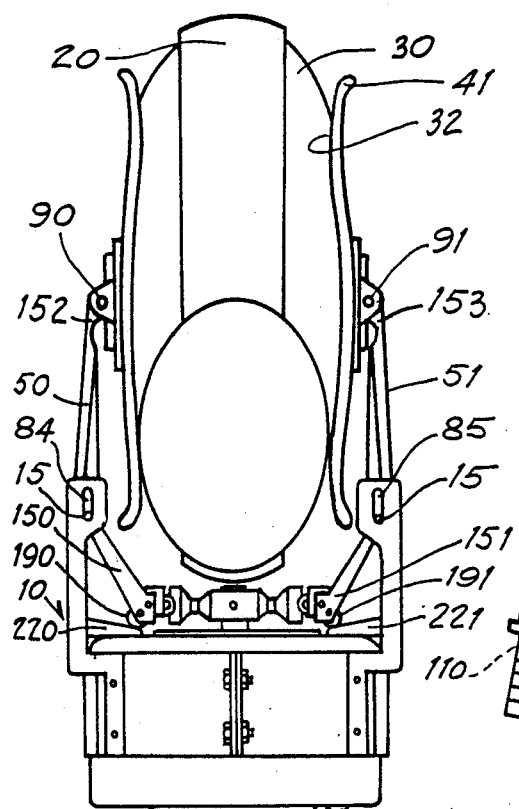
FIGS. 6–9 shows alternate form of the invention.

As FIG. 6 shows each needle bearing 92 and 93 has an end 140 that is attached to actuating levers 50 and 51 and another end 141 that rests in and is moveably retained in slots 84 and 85 of slotted arm supports 80 and 81 respectively. The lower ends 150 and 151 of the actuating levers 50 and 51 are attached to reciprocators 130 and 131 by needle bearing pairs 94 and 95 respectively.

Figure 3:
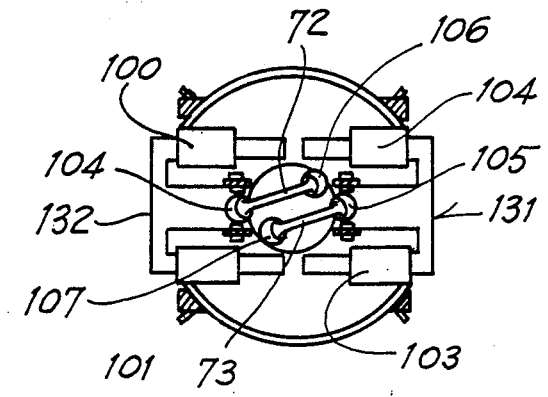
FIG. 3 is a view from line 3—3 of FIG. 1.
Figure 8:
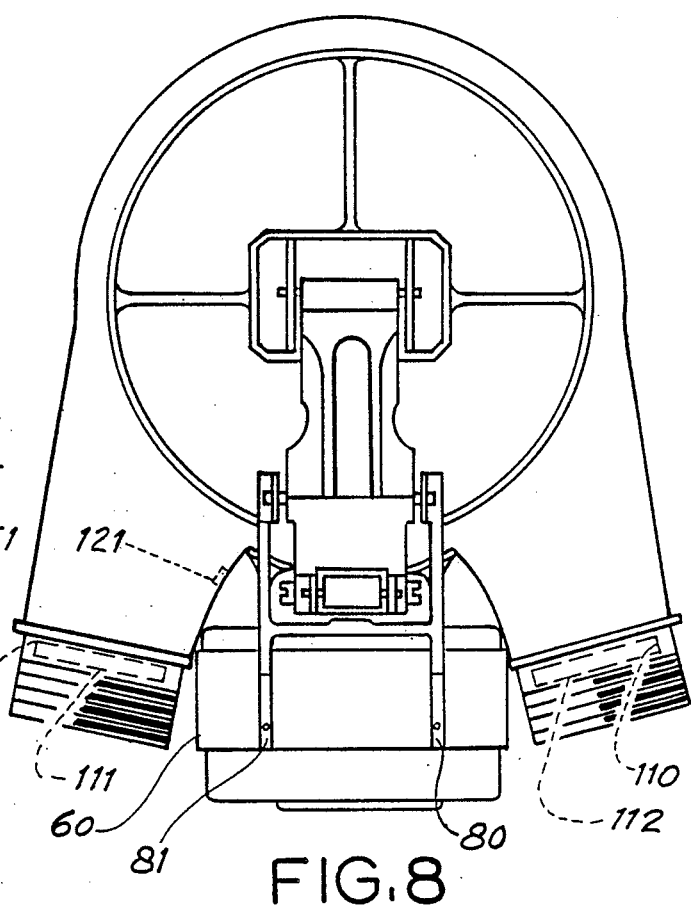
Figure 7:
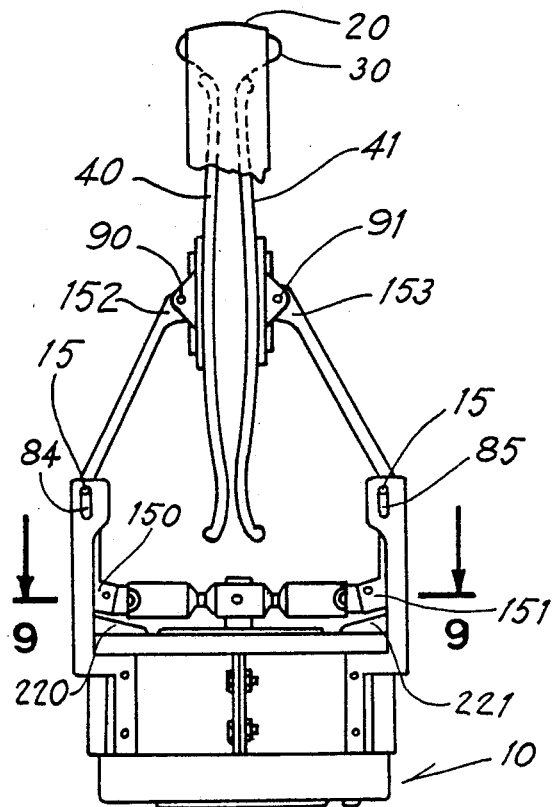

Referring now to FIG. 3 it may be seen that the lower ends of the actuating levers 50 and 51 which are attached to the E-shaped reciprocators 130 and 131 by the needle bearings 94 and 95 are also attached on either end to the L-balls 104 and 105. Each respective E-shaped reciprocator 130 and 131 is directly pivotally attached to the lower ends 150 and 151 of each actuating lever 50 and 51. The two outer bars of each E-shaped reciprocator are the linear miniature stroke ball-bearings 100 through 103. Referring back to L-balls 104 and 105; the L-balls 104 and 105 are located on the center bar 132 of each E-shaped reciprocator 130 and 131. In FIG. 8 the link arms 72 and 73 are attached to the L-balls 104–107 may be seen to run from L-balls 104 and 105 to L-balls 106 and 107. L-balls 106 and 107 are attached to the shaft 71 of the motor 70.

The L-balls 104 through 107 are bearing which, although they are attached to link arms 72 and 73, allow the link arms 72 and 73 to swivel with respect to the position of each L-ball 104 through 107. Therefore as L-balls 107 and 106 are rotated on the motor shaft 71 the L-balls 104 and 105 that are connected to the center bars 132 of the reciprocators 130 and 31 are pulled towards the motor shaft 71. This causes the actuating levers 50 and 51 to move and the position of the pusher plates 40 and 41 to turn about 150 degrees from the position shown in FIG. 5 to the position shown in FIG. 1. The reverse of the above described movement would move the pump pusher plates 40 and 41 from the position in FIG. 1 back to the position of FIG. 5. This is how the blood sac 30 is compressed and expanded.

Figure 5:
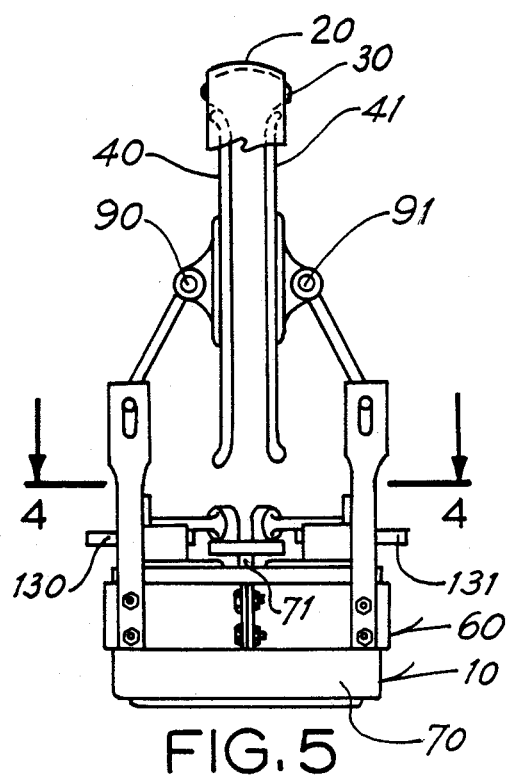
FIG. 5 is a side elevational view of the ventricular assist device, showing the blood sac (broken away) compressed.

An important feature of the invention is the connection of the pusher plates to actuating levers 50 and 51. Please see FIGS. 1-5. The actuating levers 50 and 51 move the pump pusher plates 40 and 41 in a straight line direction back and forth, but the lever still moves through an angle. Normally pushing one end of a lever will cause the ends of the lever to move in an arc and a plate fixed to such a lever will move through a corresponding angle. However because movement in an arc would distort the blood sac 30 and lead to an undesirable pumping action the pusher plates 40 and 41 are not fixed to the ends of the actuating levers 50 and 51. The pusher plates 40 and 41 are pivoted to the actuating levers 50 and 51 by needle bearings 90 and 91. In order to prevent the pusher plates 40 and 41 from moving in an arc that would distort or pull down the sides 31 and 32 of the blood sac 30 bearings 92 and 93 for each lever 50 and 51 that drives the pusher plates 40 and 41 are placed in slots 84–87, respectively, of the slotted arm supports 80–83 (see FIGS. 1 and 5 showing slots 84 and 85, and arm supports 80 and 82). Further, the levers 50 and 51 are bent at the point the needle bearing sets 92 and 94 are attached to the actuating levers 50 and 51. The angle of the bend of the actuating levers 50 and 51 is such that it provides for full compression of the blood sac 30 when the reciprocators 131 and 130 are at their maximum extension without destruction of any cells contained within the blood sac (i.e. the sides 31 and 32 of the blood sac never touch). Because the lower ends 150 and 151 of the levers 50 and 51 are pushed in a fixed straight linear path by the rotation of the motor shaft 71 through the link arms 72 and 73 and the reciprocators 130 and 131, the movable fulcrum 15 travels upward in the slots 84 through 87 until full compression stroke of the blood sac 30 is achieved. Please see FIGS. 1 and 5. Further because the lower ends 150 and 151 are constrained to a precise linear path and the fulcrum point 15 moves upward in the slots 50 and 51 that are connected to the pusher plates 40 and 41 by the needle bearings 90 and 91 move in precise linear path toward each other during systole and when the motor reverses its direction at the end of the full systole stroke the pusher plates 40 and 41 pull the sides 31 and 32 away (diastole) from each other again in a straight linear path thereby achieving maximum efficiency of the blood through the blood sac.

Figure 10:
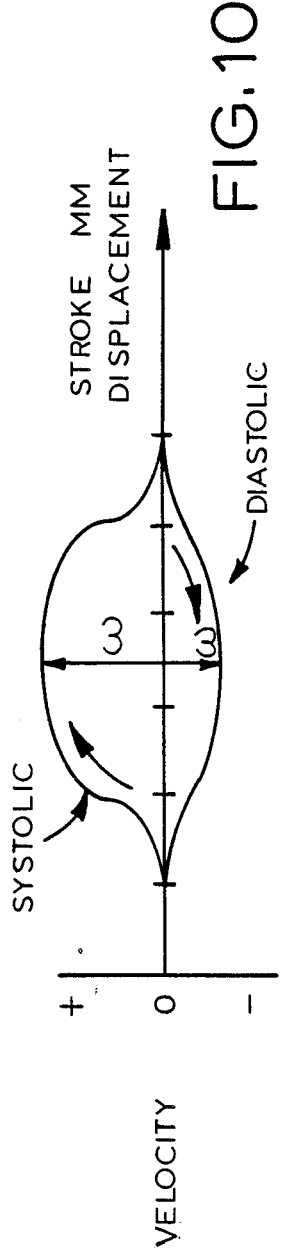
FIG. 10 is a graph showing the motion of the pusher plates of the heart assist device during systole and diastole.

The speed of each stroke of the motor 70 is controlled by a computer control circuit 120 shown in FIG. 11. The sensor 121, which may be located in the atrial valve 111 provides the microprocessor 123 with information regarding the atrial blood pressure and/or the R wave signal generated by the body which regulates the beat of the heart. This allows the computer 120 to adjust the rate of motor speed in response to the heart rate itself. Further the computer control circuit 120 is able to vary the speed of each stroke of the motor 70 during the stroke itself. The result is that the pressure of blood leaving the blood sac 30 initially is very low as the pusher plates 40 and 41 are brought together by the actuating arms 50 and 51 that are linked to the shaft 71 by the linkages 72 and 73 through the reciprocators 130 and 131, allowing the valves 111 and 112 of the device 10 to properly seat themselves before the pressure rises steeply. This process occurs in both systole and diastole and is illustrated graphically in FIG. 10. The computer control circuit 120 is able to function as it does because of a commutation code that is located in a custom IC 122 which has a Programmable Read Only Memory. This code cannot be lost by a power failure because it is contained in a non-volatile RIM IC. This code allows the microprocessor to interpret the information that it receives from the sensor 121 and provide the proper speed signal to the motor 70.

Also the commutation code contains a fail safe default instruction that allows the computer control circuit 120 to disregard the information it receives from the sensor 121 and pump blood through the heart at a predetermined fixed rate. This is especially important if the heart goes into fibrillation or stops beating.

Because the pump pusher plates 40 and 41, in conjunction with the actuating levers, both compress and expand the blood sac 30 positively, blood is continually moved into and out of the blood sac 30 and the heart itself. This means that every surface of the blood sac and the heart is continually washed thereby helping to prevent the blood from clotting.

The structure shown in FIGS. 6 through 9 shows an alternative structure that is very similar to the structures disclosed in FIGS. 1 through 5 and could also be used as a heart assist device. The major difference is in the way the motor 70 causes the lower ends 150 and 151 of the levers 50 and 51 to move.

The lower ends 150 and 151 of the levers 50 and 51 are pushed by a rotatable cam 180. The lower ends 150 and 151 of levers 50 and 51 each have a roller 190 and 191 that is pushed at controlled intervals. The rollers 190 and 191 ride on straight cam ramps 220 and 221 located at each side of the ventricular assist device 10. Please see FIGS. 6 and 8. As the lower ends 150 and 151 of each lever 50 and 51 move out to the side they also rise on the ramps 220 and 221. This pushes the movable fulcrums 15 of each lever 50 and 51 higher in the slots 84 through 87. The shape of the ramps 220 and 221 are such that the rising of each lever 50 and 51 just compensates for the arc through which the upper ends 152 and 153 of each lever 50 and 51 would normally move. This changes the motion of the upper ends 152 and 153 of each lever 50 and 51 into a precise linear or straight line motion. Thus the two levers 50 and 51 are moving simultaneously inward in a so that the two pump pusher plates 40 and 41 approach each other along the axis joining their centers. As previously described, plates 40 and 41 are pivoted to levers 50 and 51 so that they remain parallel to each other. For these reasons the blood sac 30 is not distorted but is evenly compressed as shown in FIG. 2. The pump pusher plates 40 and 41 do not quite touch as they approach each other but leave enough space in between them in the blood sac 30 so that the red and white blood cells are not put under any pressure and are not killed but remain floating freely in the plasma. Between each compression stroke the blood sac is refilled with blood because the circular cam 180 releases the ends 152 and 153 of the levers 50 and 51 thereby allowing the pressure of the blood to move blood into the blood sac 30, expanding the sac before the next compression stroke.

Figure 9:
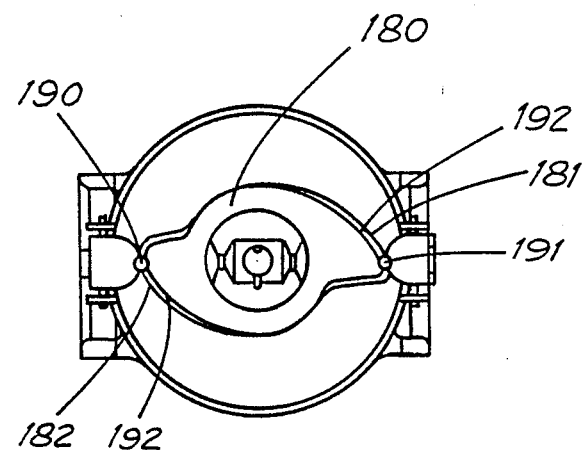

The process by which the actuating levers 50 and 51 are put into motion is best shown in FIG. 9. The motor 70 is a known brushless toroidally wound type motor which drives the cam 180 at a rate that is determined by the pick-up of the body's signal to the heart that initiates the beating of the heart and/or the atrial blood pressure. As was noted supra this signal is relayed to the motor 70 by sensor 121.

The cam 180 is shaped to provide a smooth sideways motion to the lower ends 152 and 153 of the actuating levers 50 and 51, causing the speed of each stroke of the pusher plates 40 and 41 to be, like the preferred embodiment, initially low thereby allowing the valves of the heart and the device a chance to seat themselves before the pressure of the blood flow rises thereby limiting wear and tear on the valves. The levers 50 and 51 operate through cam rollers 190 and 191 running in a channel 192 that may be seen in the edge 193 of the cam 180 in FIGS. 6 and 9. This keeps the friction between the parts as low as possible. It is necessary to have friction at a minimum because it is not possible to lubricate these parts once the assist device 10 implanted in the patient. These parts must be able to run for months unlubricated, therefore it is preferable to use the above mentioned cam roller system.

What is claimed is:

1. A heart assist device for a heart to assist it in completing successive blood pumping cycles comprising;
    a blood sac;
    at least one sensor means adapted to sense the progress of blood pumping cycles;
    computing means;
    at least one reversible motor means to power said heart assist device through successive blood pumping cycles;
    a pair of rigid plates secured to the walls of said blood sac;
    a pair of lever means each having a first lever end hingedly connected to a respective rigid plate to transmit force toward and away from said plates and a second end remote from said first end;
    said sensor means being connected to a circuit to relay information about said heart to said computing means;
    said computing means being adapted to analyze said information and send motor signals to said reversible motor means controlling the speed of said reversible motor means;
    said reversible motor means being drivingly connected to said lever means at said respective second ends of said lever means;
    said lever means each having a fulcrum moveable toward and away from the respective first ends of the respective lever means;
    fulcrum control means controlling the position of each said fulcrum as each said lever means is driven by said motor means to constrain the end of said lever means connected to a said rigid plate to move in a substantially straight line toward the center of the other rigid plate;
    said rigid plates compressing said blood sac during the compression stroke of said motor means;
    said motor means reversing direction and said rigid plates positively expanding said blood sac during the expansion stroke of said motor means;
    said expansion causing a mild suction within the blood sac;
    whereby continuous active filling and emptying of said blood sac and said heart occurs, greatly reducing the risk of clot formation, and the speed of each stroke of said motor means may be varied, during the course of each said stroke, allowing a low initial blood pressure that lets the valves of the heart and the heart assist device to properly seat themselves before the blood pressure reaches its maximum level thereby avoiding damage to the valves of the heart and ensuring a long life for the valves of the heart assist device.

2. The device of claim 1 in which said first lever ends are so dimensioned with respect to the paths of their respective second ends that said blood sac is never compressed sufficiently so that said walls of said blood sac touch.

3. The device of claim 1 in which said sensor means is adapted and positioned to detect only the atrial pressure of the blood.

4. The device of claim 1 in which said sensor means is adapted and positioned to detect the natural electrical signal that initiates each beat of said heart.

5. The device of claim 1 in which said sensor means is adapted and positioned to detect both the electrical signal that initiates each heart beat and the atrial pressure of the blood.

6. The device of claim 1 further comprising:
    said reversible motor means being a reversible brushless toroidally wound DC motor;
    said fulcrum control means comprising a plurality of linear bearings;
    a said sensor means being an atrial pressure sensor connected to relay a sensor signal corresponding to the atrial blood pressure to said computing means;
    said computing means being adapted to use said sensor signal as a reference and vary the speed of said reversible motor means accordingly;
    said lever means each being linked to said reversible motor means by links connected to said linear bearings whereby;
    said levers move said pusher plates toward and away from each other in a straight line determined by said linear bearings;
    said reversible motor means being responsive to said sensor signals to reverse direction as said plates approach most closely and to thereafter expand said blood sac during the return stroke of said reversible motor means whereby;
    said expansion causes a generally non-destructive expansion within the blood sac.

7. In a heart assist device having a generally disc shaped blood sac;
    said blood sac having two generally flat circular parallel sides having edges;
    said sides being joined in a smooth curve at said edges;
    said sides and said edges generally delineating the shape of said blood sac;
    said blood sac having two generally tubular vein-attaching structures that enter said blood sac at an angle that is generally tangent to said edges;
    the novelty comprising;
    at least a pair of generally rigid continuously parallel plates positively secured to opposite sides of said blood sac;
    motor means to drive said plates toward and away from each other; and
    connecting means connecting said motor means and said plates in a way that constrains each side plate to move in a substantially straight path toward and away from the center of another said plate.

8. The device of claim 2 in which said connecting means comprise;
    a frame;
    at least two levers;
    each said lever having a center, a plate end and a motor end;
    each said lever having a fulcrum near said center;
    each said lever having a plate pivot at said plate end connected to a said plate;
    each said lever having a drive pivot at said motor end driven by said motor means;
    said fulcrum being pivotally and slideably engaged in a slot in said frame for movement in a direction that has a component substantially at right angles to the movement of said plate.

9. The device of claim 8 further comprising a cam driven by said motor means and a cam follower on said motor end of each said lever;
    said connecting means further comprising a ramp adjacent the motor end of each said lever;

said motor end of each said lever being driven by said cam follower means along said ramp;

said motor end of each said lever being moveable up and down a said ramp whereby to move said fulcrum as said lever moves to constrain the plate end of said lever to said path;

said motor means being reversible in synchrony with the beating of said heart.

10. The device of claim 8 further comprising a symmetrical cam between said motor ends of said levers driving each of said levers;

said motor means rotating continuously;

said cam being driven by said motor means;

and sensors responsive to the patient's heart and having signal producing means producing signals whereby said signals keep said motor synchronized with the stroke of the patient's heart.

11. The device of claim 2 in which the straight paths of the respective parallel plates end at a sufficient distance from each other whereby said walls of said blood sac do not touch at their closest approach.

12. In a heart assist device having a generally disc shaped blood sac;

said blood sac having two generally flat circular parallel sides having edges;

said sides being joined in a smooth curve at said edges;

said sides and said edges generally delineating the shape of said blood sac;

said blood sac having two generally tubular vein-attaching structures that enter said blood sac at an angle that is generally tangent to said edges;

the novelty comprising;

at least a pair of generally rigid continuously parallel plates positively secured to opposite sides of said blood sac;

motor means to drive said plates toward and away from each other;

connecting means connecting said motor means and said plates in a way that constrains each said plate to move in a substantially straight path toward and away from the center of another said plate;

said connecting means comprising;

a frame;

at least two levers;

each said lever having a center, a plate end and a motor end;

each said lever having a fulcrum near said center;

each said lever having a plate pivot at said plate end connected to a said plate;

each said lever having a drive pilot at said motor end driven by said motor means;

said fulcrum being pivotally and slideably engaged in a slot in said frame for movement in a direction that has a component substantially at right angles to the movement of said plate.

13. The device of claim 12 further comprising a cam driven by said motor means and a cam follower on the motor end of each said lever;

said connecting means further comprising a ramp adjacent the motor end of each said lever;

said motor end of each said lever being driven by said cam follower means along said ramp;

said motor end of each said lever being moveable up and down a said ramp whereby to move said fulcrum as said lever moves to constrain the plate end of said lever to said path.

14. In a heart assist device having a generally disc shaped blood sac;

said blood sac having two generally flat circular parallel sides having edges;

said sides being joined in a smooth curve at said edges;

said sides and said edges generally delineating the shape of said blood sac;

said blood sac having two generally tubular vein-attaching structures that enter said blood sac at an angle that is generally tangent to said edges;

the novelty comprising;

at least a pair of generally rigid continuously parallel plates positively secured to opposite sides of said blood sac;

connecting means comprising levers having motor ends and plate ends;

a symmetrical cam between said motor ends of said levers;

motor means driving said symmetrical cam so that said plates move toward and away from each other;

said connecting means connecting said motor means and said plates in a way that constrains each said plate to move in a substantially straight path toward and away from the center of another said plate; and sensors responsive to the patient's heart and having electrical signal producing means producing signals to control said motor means whereby said signals keep said motor means synchronized with the stroke of the patient's heart.

* * * * *